United States Patent [19]
Meglin

[11] Patent Number: 6,080,178
[45] Date of Patent: Jun. 27, 2000

[54] VENA CAVA FILTER

[76] Inventor: Allen J. Meglin, 1912 Ashbrook Dr., Wilmington, N.C. 28403-5302

[21] Appl. No.: 09/408,467

[22] Filed: Sep. 28, 1999

Related U.S. Application Data

[60] Provisional application No. 60/129,955, Apr. 20, 1999, and provisional application No. 60/134,664, May 18, 1999.

[51] Int. Cl.⁷ .................................................. A61B 17/00
[52] U.S. Cl. .......................................................... 606/200
[58] Field of Search .................................. 606/200, 169, 606/198, 191, 199, 127

[56] References Cited

U.S. PATENT DOCUMENTS

| | | | |
|---|---|---|---|
| 3,952,747 | 4/1976 | Kimmell, Jr. | 128/303 R |
| 4,425,908 | 1/1984 | Simon | 128/1 R |
| 4,494,531 | 1/1985 | Gianturco | 128/1 R |
| 4,553,545 | 11/1985 | Maass et al. | 128/341 |
| 4,643,184 | 2/1987 | Mobin-Uddin | 128/303 R |
| 4,655,771 | 4/1987 | Wallsten | 623/1 |
| 4,662,885 | 5/1987 | DiPisa, Jr. | 623/12 |
| 4,727,873 | 3/1988 | Mobin-Uddin | 128/303 R |
| 4,793,348 | 12/1988 | Palmaz | 128/325 |
| 4,817,600 | 4/1989 | Herms et al. | 128/303 R |
| 4,832,055 | 5/1989 | Palestrant | 128/899 |
| 4,943,297 | 7/1990 | Saveliev et al. | 606/200 |
| 4,957,501 | 9/1990 | Lahille et al. | 606/200 |
| 4,969,891 | 11/1990 | Gewertz | 606/200 |
| 4,990,156 | 2/1991 | Lefebvre | 606/200 |
| 5,059,205 | 10/1991 | El-Nounou et al. | 606/200 |
| 5,147,370 | 9/1992 | McNamara et al. | 606/108 |
| 5,147,379 | 9/1992 | Sabbaghian et al. | 606/206 |
| 5,151,105 | 9/1992 | Kwan-Gett | 623/1 |
| 5,197,978 | 3/1993 | Hess | 623/1 |
| 5,242,462 | 9/1993 | El-Nounou et al. | 606/200 |
| 5,324,304 | 6/1994 | Rasmussen | 606/200 |
| 5,344,427 | 9/1994 | Cottenceau | 606/200 |
| 5,350,398 | 9/1994 | Pavcnik et al. | 606/200 |
| 5,370,657 | 12/1994 | Irie | 606/200 |
| 5,375,596 | 12/1994 | Twiss et al. | 128/653.1 |
| 5,413,586 | 5/1995 | Dibie et al. | 606/200 |
| 5,415,630 | 5/1995 | Gory et al. | 604/53 |
| 5,421,832 | 6/1995 | Lefebvre | 604/53 |
| 5,484,424 | 1/1996 | Cottenceau et al. | 604/282 |
| 5,513,637 | 5/1996 | Twiss et al. | 128/653.1 |
| 5,531,788 | 7/1996 | Dibie et al. | 623/11 |
| 5,595,909 | 1/1997 | Hu et al. | 435/297.4 |
| 5,601,568 | 2/1997 | Chevillon et al. | 606/108 |
| 5,601,595 | 2/1997 | Smith | 606/200 |
| 5,626,605 | 5/1997 | Irie et al. | 606/200 |
| 5,634,942 | 6/1997 | Chevillon et al. | 623/1 |
| 5,649,906 | 7/1997 | Gory et al. | 604/53 |
| 5,704,910 | 1/1998 | Humes | 604/52 |
| 5,720,764 | 2/1998 | Naderlinger | 606/200 |
| 5,746,767 | 5/1998 | Smith | 606/200 |
| 5,766,160 | 6/1998 | Samson et al. | 606/1 |
| 5,769,816 | 6/1998 | Barbut et al. | 604/96 |
| 5,800,457 | 9/1998 | Gelbfish | 606/200 |
| 5,807,398 | 9/1998 | Shaknovich | 606/108 |
| 5,836,968 | 11/1998 | Simon et al. | 606/200 |
| 5,836,969 | 11/1998 | Kim et al. | 606/200 |
| 5,848,964 | 12/1998 | Samuels | 600/200 |
| 6,007,558 | 12/1999 | Ravenscroft et al. | 606/200 |
| 6,013,093 | 1/2000 | Nott et al. | 606/200 |

OTHER PUBLICATIONS

Bonn J, Liu J, Eschelman DJ, Sullivan KL, Pinheiro LW, Gardiner GA. Intravascular ultrasound as an alernative to positive–contrast vena cavography prior to filter placement. J Vasc Surg 1999; 10:843–849.

Neuzil DF, Garrard CL, Berkman RA, Pierce R, Naslund TC. Duplex–directed vena caval filter placement: Report of initial Experience. Surgery 1998; 123:470–4.

*Primary Examiner*—Michael Buiz
*Assistant Examiner*—Kevin Truong
*Attorney, Agent, or Firm*—Wolf, Greenfield & Sacks, P.C.

[57] ABSTRACT

A vena cava filter and placement set includes features which can be visualized solely utilizing sonography. A method of implanting a vena cava filter employs sonography to enable the surgeon to direct the filter to a desired location and ensure that the filter is properly deployed.

20 Claims, 13 Drawing Sheets

VENA CAVA FILTER

RELATED APPLICATIONS

This application is related to provisional U.S. patent applications Ser. Nos. 60/129,955 and 60/134,664, filed Apr. 20, 1999 and May 18, 1999, respectively, both incorporated herein in their entirety by reference.

BACKGROUND

1. Field of the Invention

The present invention relates generally to implantable blood filters. More particularly, the invention relates to caval filters having sonographically conspicuous features.

2. Related Art

Advances in many surgical specialties have saved the lives of many patients suffering serious illness or injury, and have improved the quality of life of countless others. However, such surgical repair of organs and tissues can disrupt the body's plumbing, e.g., the circulatory system, sufficiently to give rise to new risks. For this reason, minimally invasive techniques have been developed, for example wherein highly specialized surgical tools are manipulated from outside a patient's body through a catheter or tube inserted through a tiny incision or puncture and guided to a surgical site. Yet, both invasive and minimally invasive procedures disturb circulation sufficiently so that arterial plaques can become dislodged or clots can form in the bloodstream and move with the circulation with the body. Such debris, moving along with normal circulation, can become lodged in and partially or completely block vessels supplying blood and oxygen to critical organs, such as the heart, lungs and brain.

Medication is often used to reduce the likelihood of blood clot formation during and after surgery, however, post-operative thrombosis, as such blood clot formation is called, remains an important problem to be solved. Therefore, filters implantable in a patient's body using minimally invasive techniques have been developed. By appropriately positioning such filters, dangerous blood clots can be removed from circulation and held in a safe location until they can be dissolved by medication or extracted, again using minimally invasive techniques. Thus, there has been a significant reduction in the incidence of morbidity and mortality due to post-operative embolism which occurs when a thrombolus moves from its site of formation to block a vessel, becoming an embolus.

Conventional implantable blood filters employing a variety of geometries are known. Many are generally basket or cone shaped, in order to provide adequate clot-trapping area while permitting sufficient blood flow. Also known are filters formed of various loops of wire, including some designed to partially deform the vessel wall in which they are implanted.

Along with their many functional shapes, conventional filters may include other features. For example, peripheral loops or arms may be provided to perform a centering function so that a filter is accurately axially aligned with the vessel in which it is implanted. In order to prevent migration under the pressure induced by normal circulation, many filters have anchoring features. Such anchoring features may include sharp points, ridges, etc. Finally, conventional filters are known which have specific features for facilitating implanting and extracting using catheterization. Thus, a surgeon can select from a variety of conventional filters, to optimize one or another parameter of interest, and implant or extract that filter using minimally invasive techniques.

The minimally invasive techniques mentioned above require that a surgeon guide a catheter to a precise location within a patient's body. The precise location within the body is visualized using conventional x-ray imaging and marked on the patient's body with marker or using x-ray fluoroscopy during surgery. The position of the catheter or other instrument within the body is visualized using similar techniques. As is well-known, x-rays, a form of ionizing radiation, produce an image showing by variations in image density corresponding variations in transmission density indicative of the position of various anatomical structures and of the instrument introduced into the body by the surgeon. In order to improve the fluoroscopic image of soft tissues, such as blood vessels, contrast media are sometimes introduced into a vessel to be imaged. An instrument which might otherwise be radiologically transparent may also be given a radiopaque tip or other feature. However, exposure to ionizing radiation or contrast media is contraindicated for a significant number of patients, such as pregnant women or patients exhibiting anaphylactic reactions to contrast media.

SUMMARY OF THE INVENTION

What is desired is a filter which is implantable in vivo in a human blood vessel, without the problems or disadvantages noted above.

In one embodiment, the invention may be realized in a filter, implantable in a blood vessel solely by sonographic visualization. Such a filter may include one or more wires arranged to trap blood clots without substantially interfering with normal blood flow; and an echogenic feature on at least one wire located in a position which during deployment of the filter remains fixed relative to one end thereof, so the filter position can be accurately determined solely by sonographic visualization. In such a filter, the echogenic feature may, for example, be a bead or a tube. When the feature is a tube, a marker wire may pass through the echogenic tube. The marker wire may include a plurality of echogenic markers, whereby correct visualization in a sonogram of a true longitudinal slice along the filter axis is readily ascertainable by presence in the sonogram of the tube in its entirety and each of the plurality of echogenic markers. Alternatively, depending on the design of the tube and its appearance in a sonogram, correct visualization in a sonogram of a true longitudinal slice along the filter axis is readily ascertainable by presence in the sonogram of the tube in its entirety.

Filters embodying the invention may be characterized by several different geometries. For example, in one geometry, one or more wires are arranged to define a cone-shaped basket attached to the echogenic feature at a vertex. The wire may be further arranged to define a substantially coplanar flower, the echogenic feature attached thereto at a center thereof. The cone and flower geometries may be combined, being joined by an outer ring of wire connecting a base of the cone to an outer position of the flower. The basket may be defined by substantially radially extending wires or by a mesh of wires extending in both radial directions and directions transverse the radial directions. Visibility using sonography of various geometries using the cone may be further enhanced by a plurality of echogenic markers substantially at a periphery of a base of the cone.

Filters embodying the invention may include other enhancements, as well. For example, the filter may include a plurality of loops of wire at a periphery of the basket, whereby the basket is axially aligned thereby during deployment thereof. The filter may also include a plurality of echogenic markers substantially at a periphery of the filter, whereby deployment thereof can be visualized.

According to another aspect of the invention, there is a method of implanting a blood filter in a blood vessel, comprising steps of: moving a blood filter having an echogenic feature located in a position which during deployment of the filter remains fixed relative to one end thereof through the blood vessel to an implantation site in the blood vessel; and during the step of moving, visualizing the echogenic feature of the filter and the implantation site sonographically. This method may be enhanced by adjusting a sonographic transducer to correctly visualize in a sonogram a true longitudinal slice along the filter axis, which is readily ascertainable by presence in the sonogram of at least one echogenic feature of the filter.

According to yet another aspect of the invention, a caval filter placement set includes a guide wire, a dilator, a sheath for introducing the filter, a caval filter including one or more wires arranged to trap blood clots without substantially interfering with normal blood flow, and an echogenic feature on at least one wire located in a position which during deployment of the filter remains fixed relative to one end thereof, so the filter position can be accurately determined solely by sonographic visualization. Moreover, the guide wire may be bent to facilitate locating a renal vein.

These and other features, objects and advantages of the invention will become apparent upon reading the following detailed description of some embodiments thereof, in connection with the drawings.

DESCRIPTION OF THE DRAWINGS

In the drawings, in which like reference designations indicate like elements.

DESCRIPTION

The present invention will be better understood upon reading the following description of several embodiments thereof, in connection with the drawings.

The present invention may be embodied in a set of devices for delivery of a caval filter to a desired position in a patient's body, preferably absent the use of fluoroscopic guidance. A caval filter embodying aspects of the invention is constructed of nitinol wire, in a form which is compact at room ambient temperature, but which expands to an operating configuration at a patient's body temperature. Alternatively, stainless steel, titanium, or other known materials implantable in the human body can be used. The filter includes a sonographically conspicuous feature at a distal, leading end thereof, by which the filter can be guided into position solely by use of sonographic imaging. As used herein, a sonographically conspicuous feature is one whose sonographic image, density, shape, etc. contrasts significantly with the image produced by other features. In order to improve the accuracy of positioning using the sonographically conspicuous feature at the distal end of the filter, the filter geometry and deployment apparatus is defined in such a way as to avoid foreshortening or other movement of the distal end of the filter during deployment. Also, sonographically conspicuous features may be included on the guide wire by which the filter is inserted and positioned in the patient's body.

Filters embodying the invention can also include sonographically conspicuous features located at the periphery of the filter. These features may be located at or near either end of the filter, depending on the design of the filter. Placing sonographically conspicuous features at the peripheral ends of the filter struts allows the opening of the filter to be observed using sonographic imaging only, if so desired. These peripheral, sonographically conspicuous features can mark the ends of filter struts or crossbars, as well as the ends of the filter. The ends of the filter can also be marked separately, as described above.

One type of sonographically conspicuous feature is one which is highly echogenic. A highly echogenic feature reflects a substantial portion of the ultrasound energy directed at it at a frequency of interest. A rough surface finish, having numerous acoustic interfaces, is more echogenic than a smoother surface finish. Also, a larger surface is more echogenic than a smaller one having a similar surface finish. Conventional bent-wire designs have been found not to be sonographically apparent.

Filters according to the principles of the present invention may be permanently implantable, e.g., having hooks to keep the filter in place, or may be removable, e.g., relying solely on pressure to keep the filter in place. Such filters can also have a variety of shapes suitable for their filtering purpose, as is known in the art. One preferred filter has an inverted cone-shaped basket at the proximal end thereof, for filtering. Some illustrative embodiments are now described in connection with the accompanying Figures.

Figure 1:
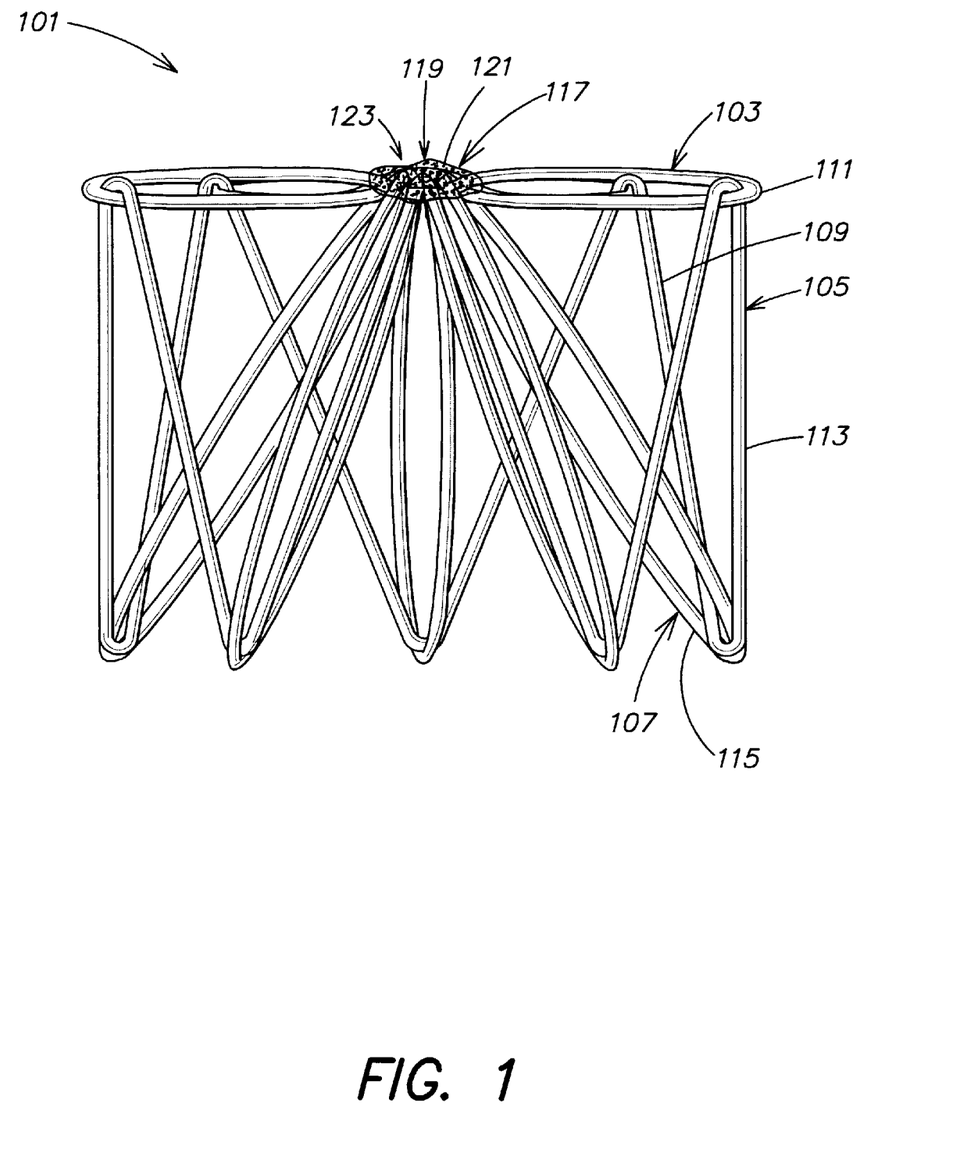
FIG. 1 is a side view of one embodiment of a filter according to some aspects of the invention.
Figure 2:
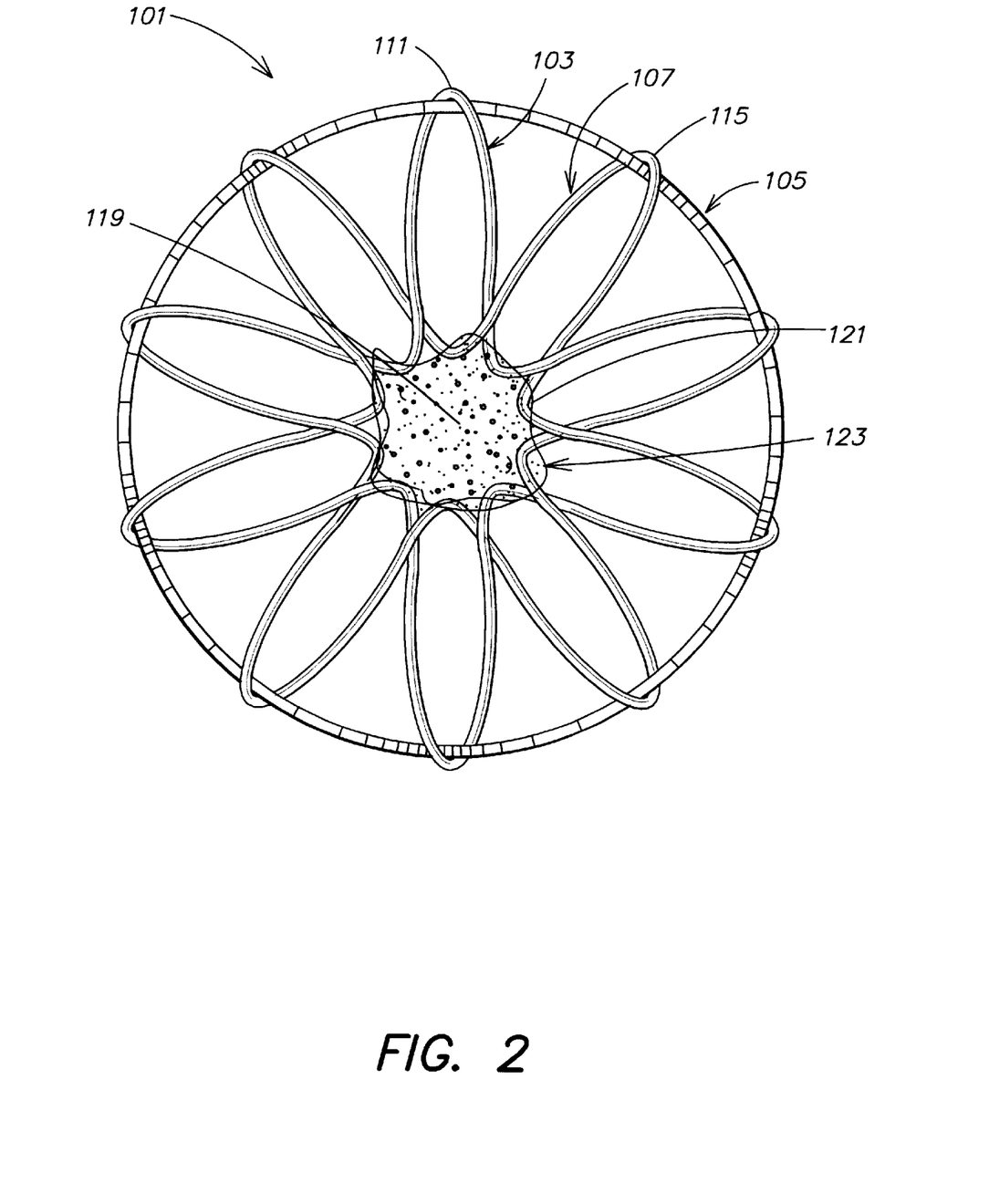
FIG. 2 is a top view of the embodiment of FIG. 1.

The side view of FIG. 1 and the top view of FIG. 2 show one filter 101 having an echogenic feature located as described above. Three continuous strands of nitinol wire 103, 105, 107 form the illustrated filter 101. The upper strand 103 is coiled into an upper flower form having five loops 111. The lower strand 107 is coiled into a lower cone form, also having five loops 115. Finally, the middle strand 105 is coiled into an outer ring having ten loops, five directed up 109 and five directed down 113.

The upper loops 109 of the middle strand 105 join the loops 111 of the upper strand 103; the lower loops 113 of the middle strand 105 join the loops 115 of the lower strand 107. The lower cone formed by the lower strand 107 has a vertex 117 joined to the center 119 of the upper flower formed by the upper strand 103 at weld 121. Weld 121 defines an echogenic bead 123. Preferably weld 121 has a diameter of 2 mm, although the diameter may also be as small as about 1 mm or even as large as about 3 mm. The diameter should be sufficient to define the echogenic bead 123 so as to provide adequate sonographic conspicuousness.

Filter 101 of this embodiment is preferably about 3 cm long and about 3 cm in diameter when fully expanded. In use, the filter may not expand fully, slight compression holding it in place where the surgeon desires.

Various alternative filter design features are now described in connection with FIGS. 3–7. These figures show various features which can be combined in numerous other permutations and combinations than shown, as will be apparent to those skilled in this art.

Figure 3:
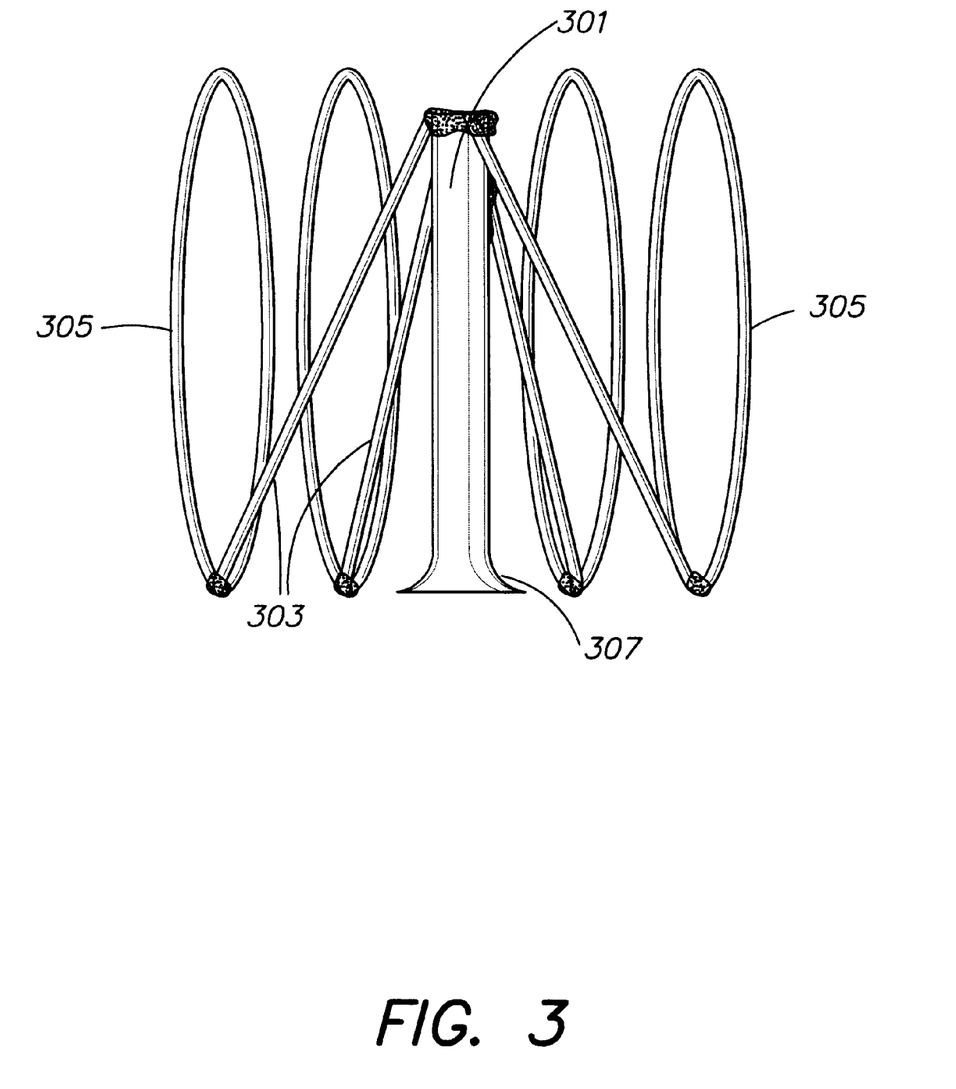
FIG. 3 is a side view of another embodiment of a filter according to aspects of the invention.

The side view of FIG. 3 shows alternative configurations for an echogenic feature and for centering features. In this alternative configuration, an echogenic tube 301 supports individual wire strands 303 arranged as a cone filter. Wire strands 303 further support individual centering loops 305. The components are welded or brazed together using conventional techniques. Echogenic properties are imparted to the tube 301 by virtue of its size and surface finish, as described above. In preferred configurations using an echogenic tube 301, the tube 301 has an inside diameter large enough to freely pass a 0.035 inch (0.89 mm) diameter guidewire. Also preferred in some configurations, the tube 301 has a flared, dilated or contracted feature 307 at one end to facilitate gripping of the tube 301 for purposes of removing the filter after it has served its purpose.

Figure 4:
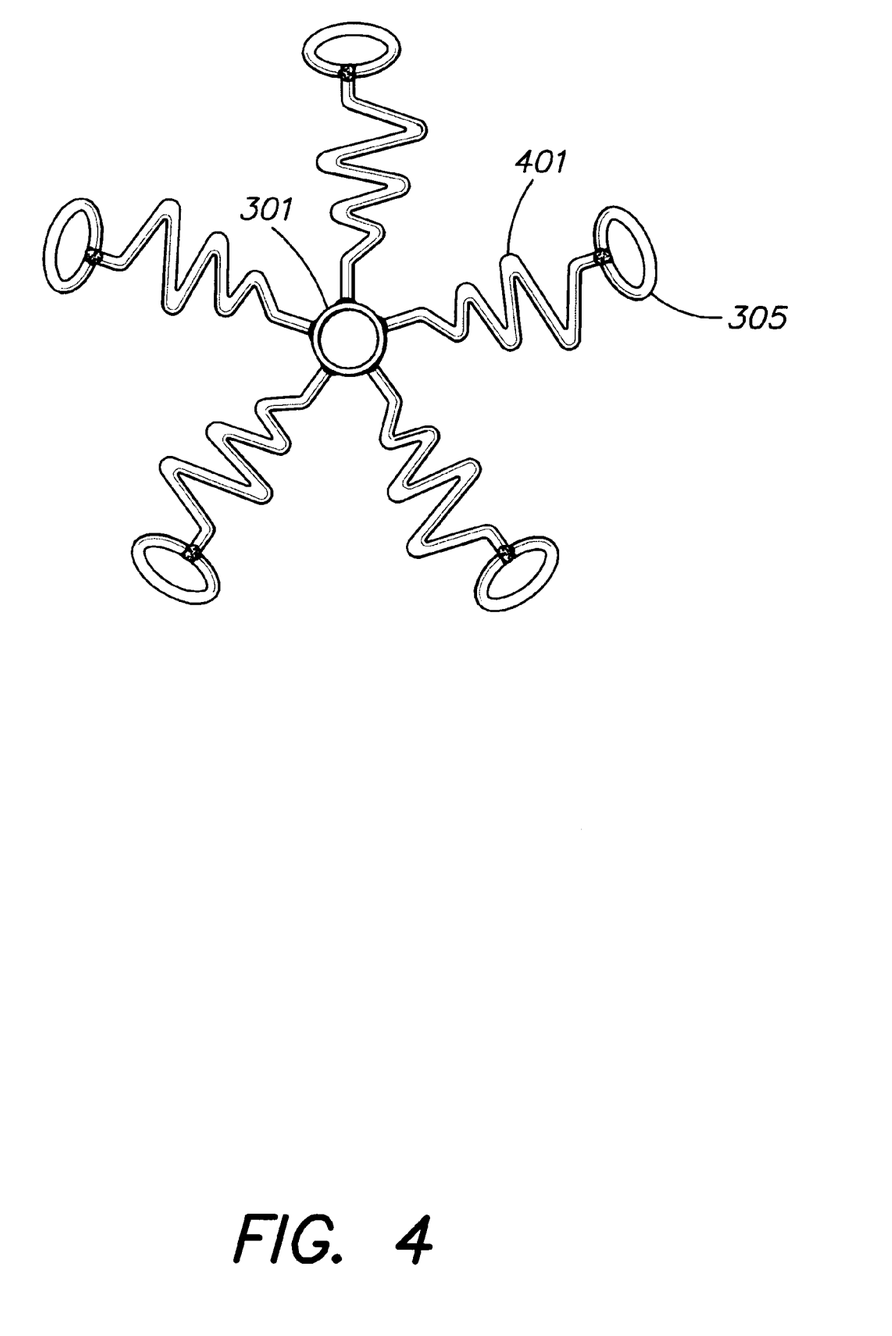
FIG. 4 is a top view of yet another embodiment of a filter according to aspects of the invention.

Although FIGS. 1–3 show filter wires (e.g., 107, 303) which are generally straight or smooth curves, as shown in FIG. 4, bent filter wires 401 can reduce the size of openings between wires, resulting in a more effective filter, without blocking the free flow of normal blood.

Figure 5:
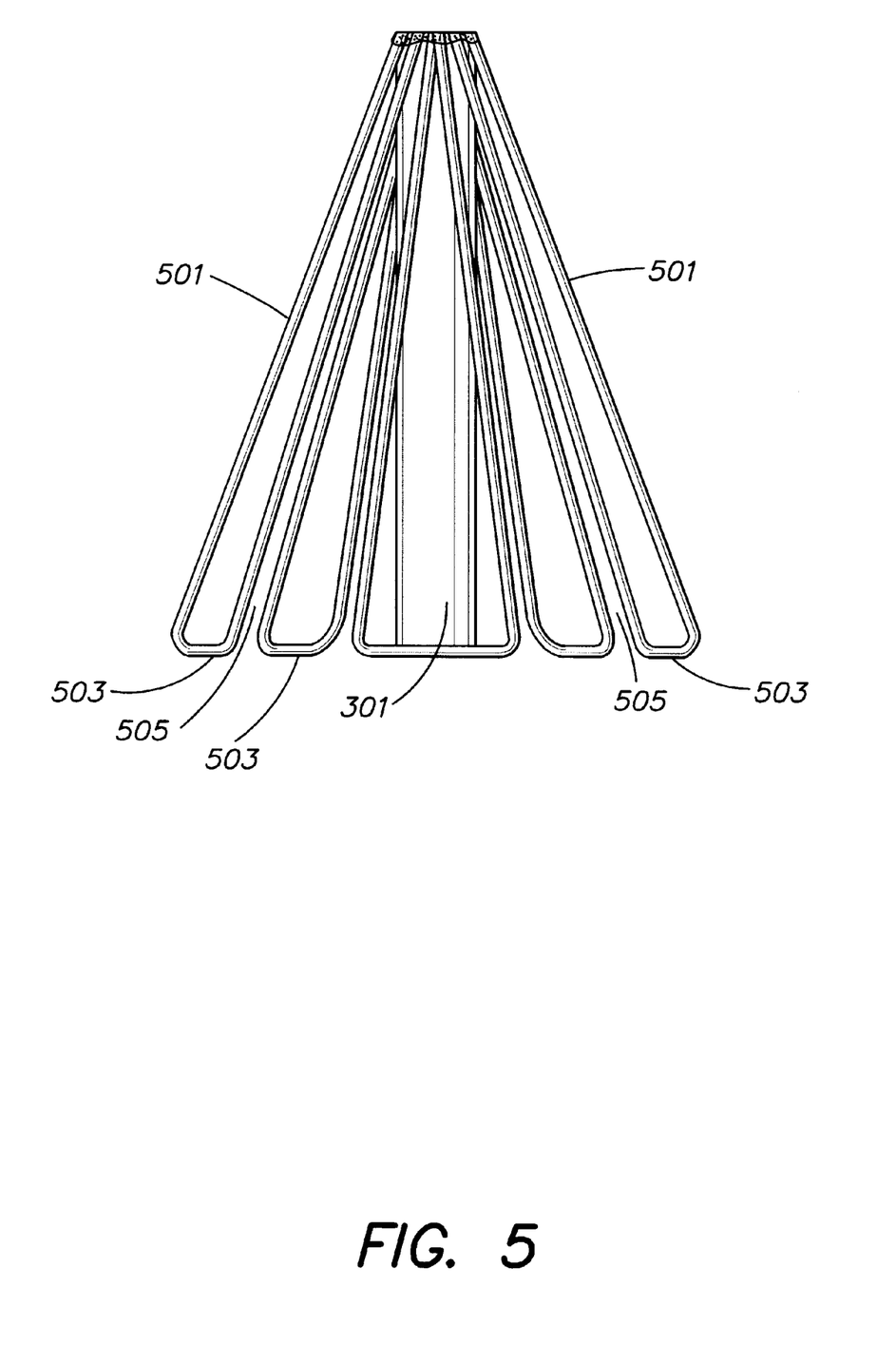
FIG. 5 is a side view of yet another embodiment of a filter according to aspects of the invention.
Figure 6:
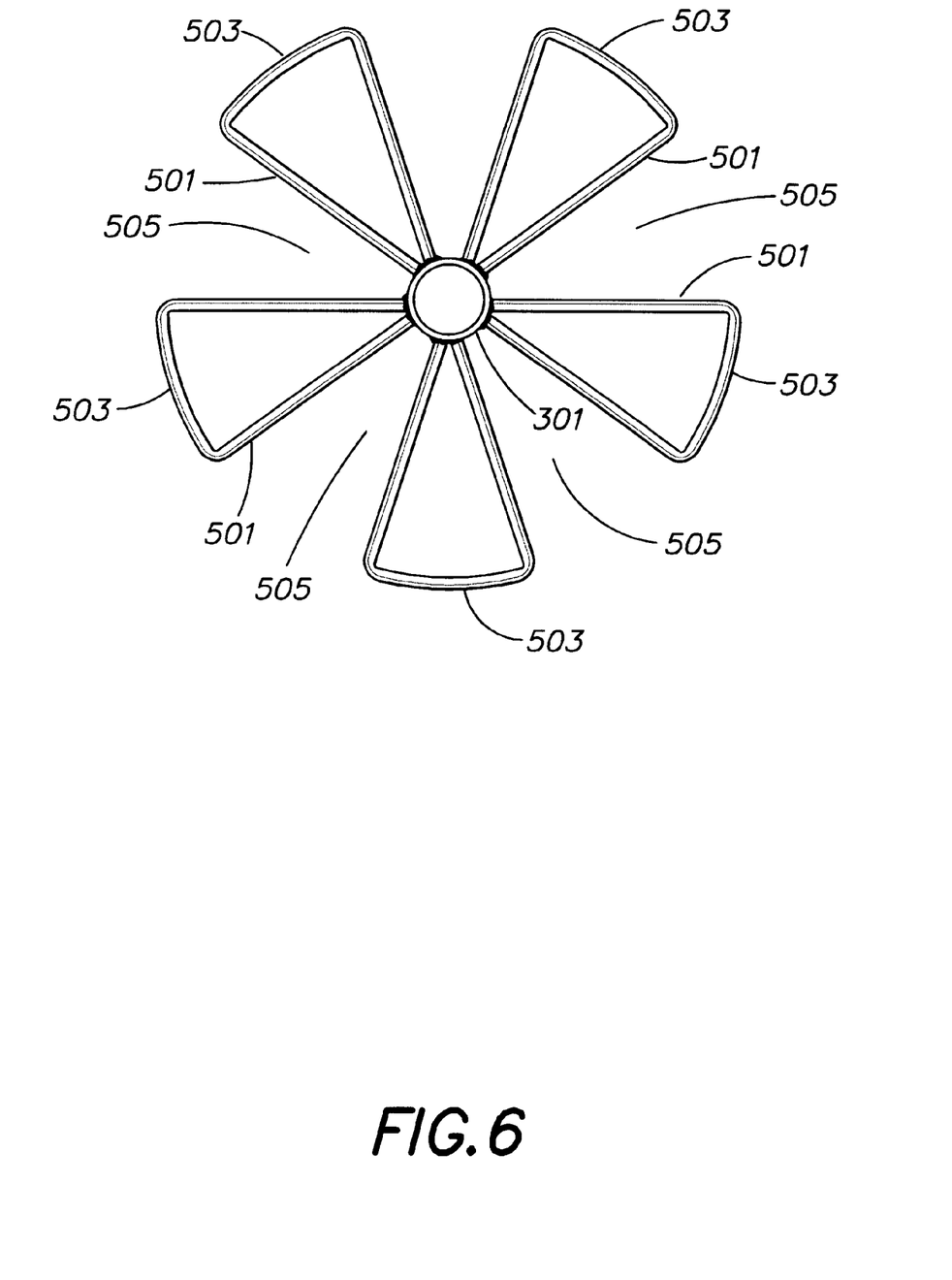
FIG. 6 is a top view of the embodiment of FIG. 5.

FIGS. 5 and 6, side and top views, respectively, illustrate a configuration employing an echogenic tube 301, as described above, to which straight filter wires 501 are conventionally welded or brazed. Instead of centering loops 305, this configuration has a split side ring 503 to prevent filter migration, once placed where desired by the surgeon. Spring pressure pushes the split side ring 503 into the vessel wall when the filter is in the position desired, thus anchoring the filter against the pressure of blood flow through the filter. Gaps 505 between segments of the split side ring 503 allow the filter to be compressed to a smaller diameter than when deployed for insertion, removal or positioning within a vessel of a patient's body. Instead of straight filter wires 501, this configuration can use bent filter wires 401, as in the configuration of FIG. 4. The echogenic tube 301 can have the characteristics and features described above in connection with FIG. 3, if desired.

Figure 7:
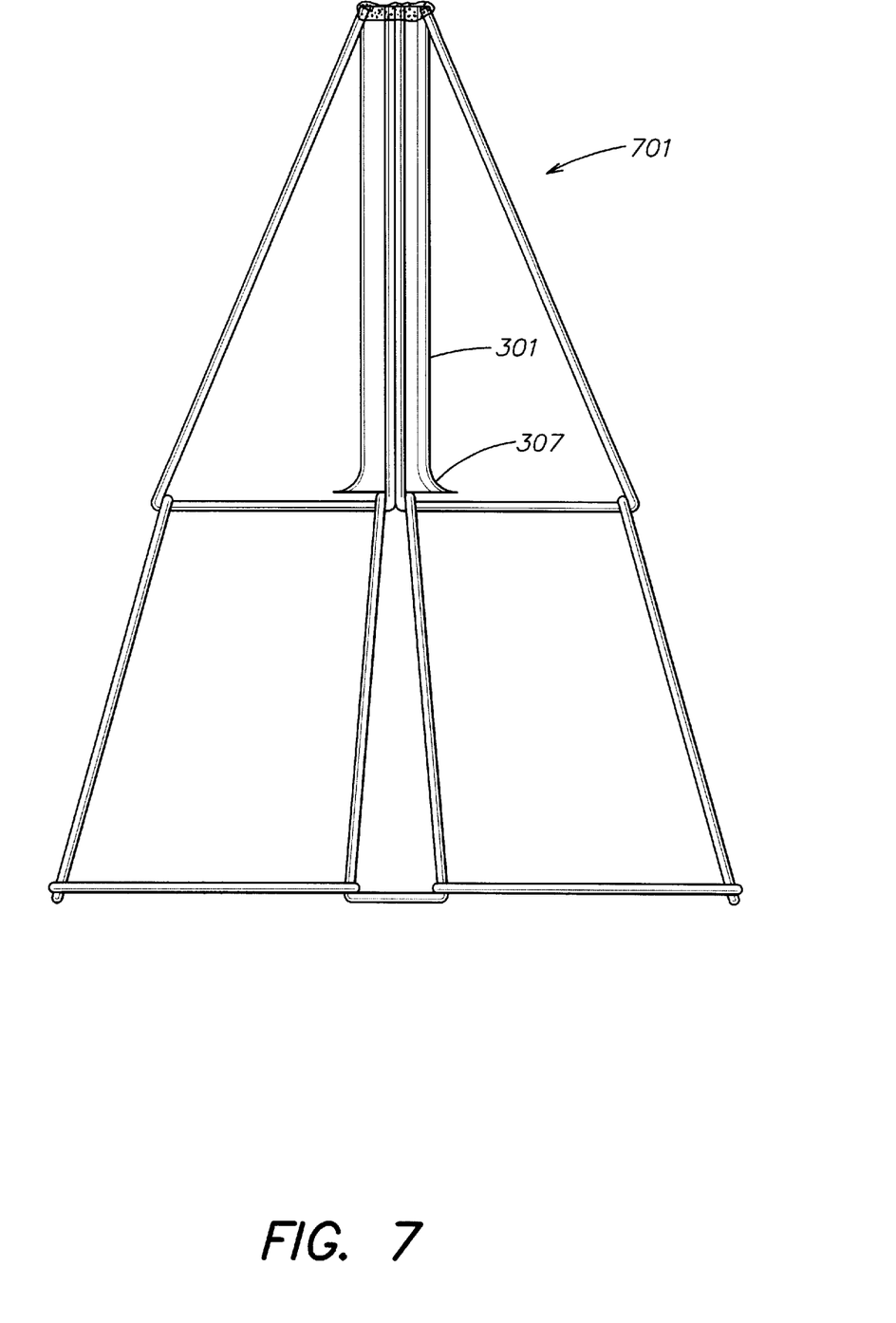
FIG. 7 is a side view of a modification of a conventional filter embodying aspects of the invention.

A modification of a conventional filter design made by MediTech, Boston Scientific (Natick, Mass.) is illustrated in the side view of FIG. 7. In this configuration, filter 701 includes an echogenic tube 301 not found in the conventional MediTech design. The echogenic tube 301 of this configuration also may include the features described above, such as the extraction feature 307.

Figure 8:
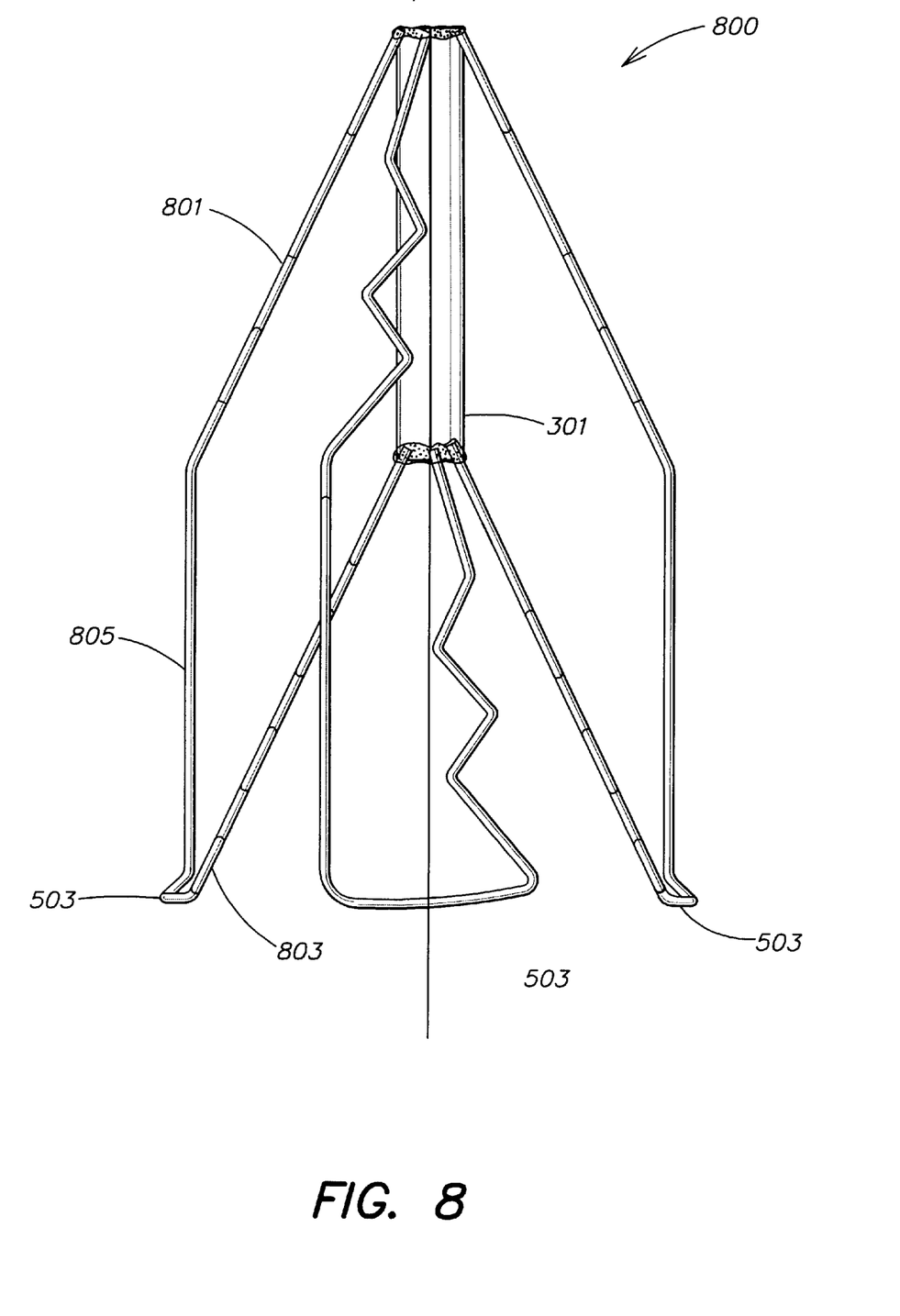
FIG. 8 is a side view of one embodiment of a filter according to some aspects of the invention.
Figure 9:
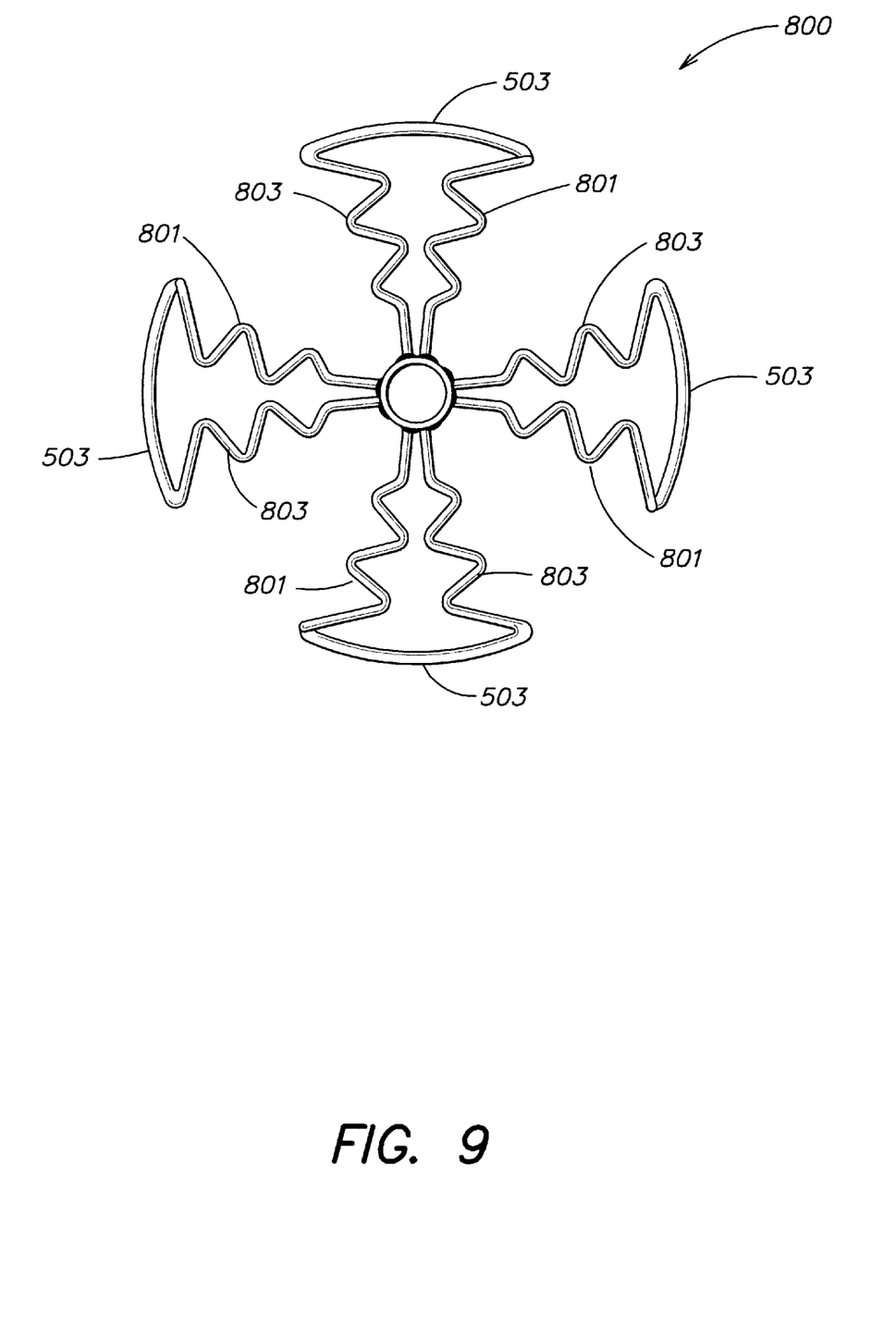
FIG. 9 is a top view of the embodiment of FIG. 8.

Yet another filter configuration is shown in FIGS. 8 and 9 in side and top view, respectively. The filter 800 shown has a central echogenic tube 301, supporting a plurality of bent wires 801, 803. Bent wires 801 are arranged as one filter cone, while bent wires 803 are arranged as a second filter cone. Bent wires 801 and 803 are connected together through straight wires 805 and a split side ring 503, similar to that described above in connection with FIGS. 5 and 6.

Figure 10:
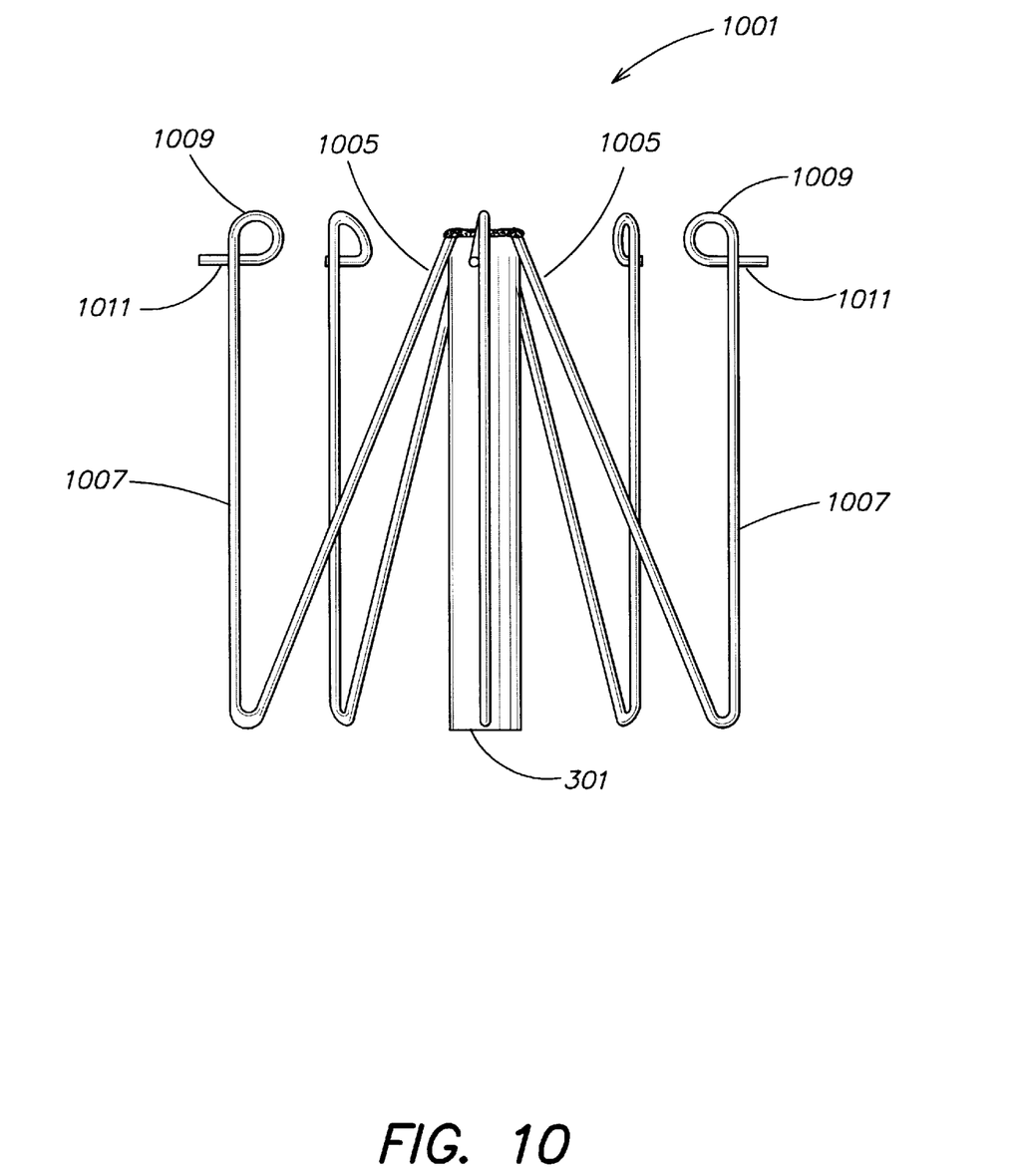
FIG. 10 is a side view of one embodiment of a filter according to some aspects of the invention.
Figure 11:
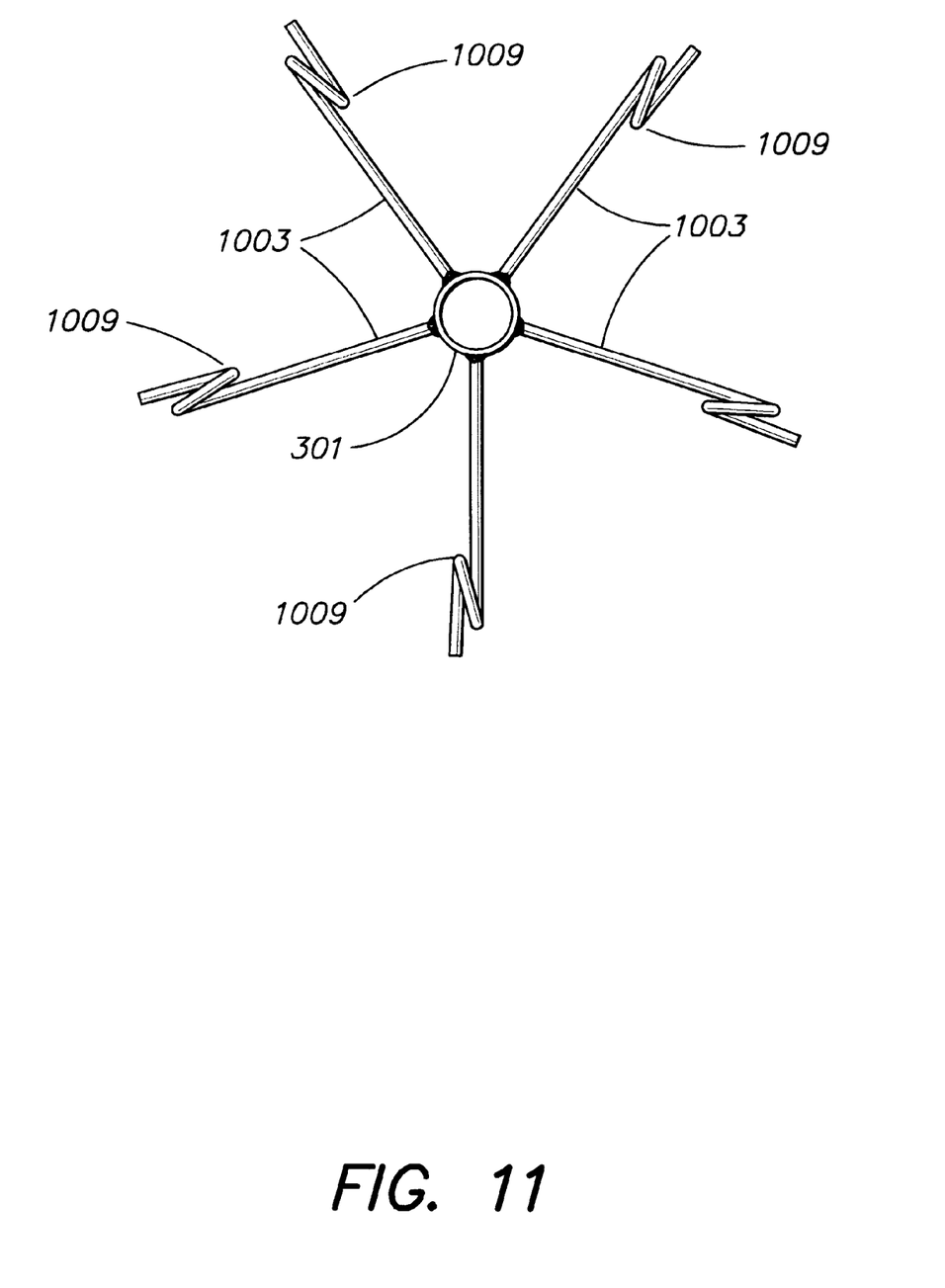
FIG. 11 is a top view of the embodiment of FIG. 10.

Finally, a simple filter is shown in FIGS. 10 and 11 in side and top view, respectively. This filter 1001 also has a central echogenic tube 301, supporting a plurality of wire legs 1003. Wire legs 1003 each have a radially extending portion 1005, arranged to form a filter cone, and a longitudinally extending portion 1007. The longitudinally extending portion 1007 centers and axially aligns the filter with the axis of the vessel in which it is to be implanted, similar to the action of centering loops 305 and the middle strand 105 of the above described embodiments. The longitudinally extending portions 1007 end in loops 1009 and points 1011, which securely anchor the filter in the vessel in which it is implanted.

Filters embodying aspects of the invention are generally used in the same manner as other filters used in this art. However, the imaging used in connection with embodiments of the invention can be sonographic, rather than fluoroscopic.

The invention can be embodied in a complete set using any of the above-described filters or variations. The set employs a #7 or #8 French dilator having an echogenic tip. The set further includes a #8 French sheath, also having an echogenic tip, of flexible plastic. Finally, the set is guided by a 0.035 inch (0.89 mm) diameter guide or marker wire having one or more, preferably three, echogenic sites at or near the distal end thereof. The guide or marker wire may be a straight wire or a curved wire, as described below in connection with FIGS. 12–14. The set thus described can be used to implant a filter using only external sonography or a combination of external sonography with other techniques, as described below. Although components of the set may be separately available, it is expect that the dilator, sheath, guide wire end filter will be supplied as a complete set also, for convenience and consistency.

Delivery and deployment of a filter, e.g., FIG. 1, 101, having an echochenic lead 123, below the renal veins proceeds as follows.

The locations of the renal veins are determined and marked on the skin with marker, using any conventional means. This may include the techniques for internal sonography described by Bonn et al., *Intravascular Ultrasound as an Alternative to Positive-contrast Vena Cavography prior to Filter Placement*, Journal of Vascular Interventional Radiology, Vol. 10, No. 7, pp. 843–849, 1999. Alternatively, external sonography can also be used to locate the renal veins.

Figure 12:
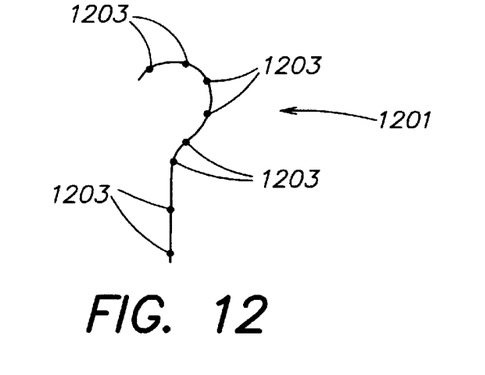
FIG. 12 is a side view of a bent guide or marker wire.
Figure 13:
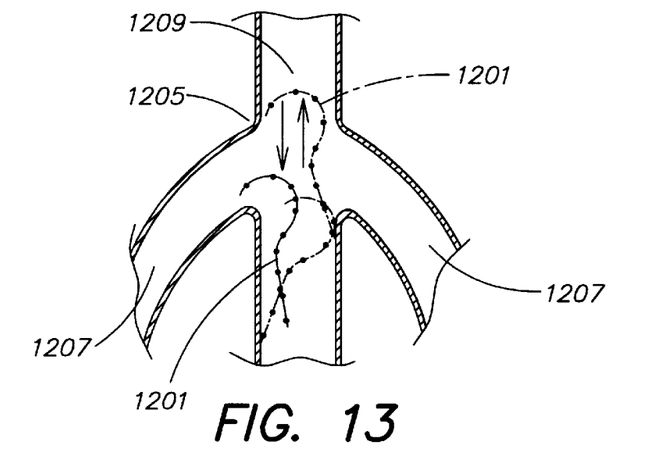
FIGS. 13 and 14 are side views showing placement of the bent guide wire in the vicinity of the renal veins within the vena cava.
Figure 14:
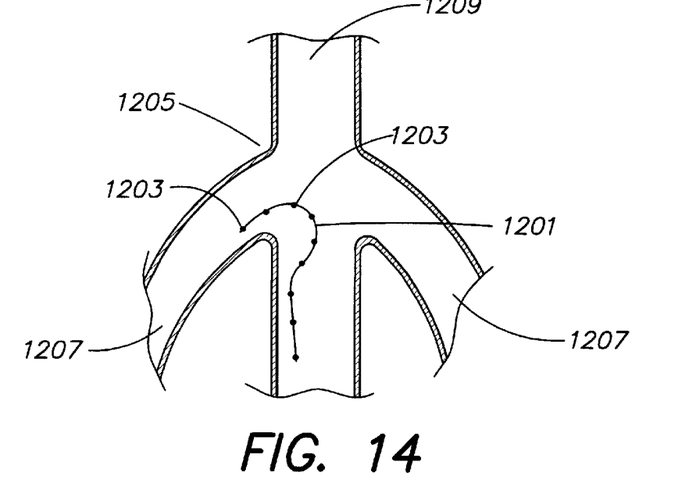

As shown in FIGS. 12–14, a curved guide wire 1201 having a series of sonographically conspicuous features 1203, for example 3–12 features spaced about 1 cm apart, is then inserted to a point just past the confluence 1205 of the renal veins 1207 forming the vena cava 1209, and then withdrawn to engage one renal vein 1207. Once the wire 1201 engages the renal vein 1207, slight advancement anchors the renal vein 1207. The progress of the curved, sonographically conspicuous wire 1201 is easily followed using external sonography.

The guide wire, particularly the curved guide wire 1201 introduced as described above, and the echogenic features of the guide wire make possible very precise identification using external sonography of the desired placement location. The dilator is then introduced over the guide wire and the echogenic tip thereof is also followed by external sonography to the filter placement location. Finally, the filter, contained in the end of the sheath, is guided over the guide wire, inside of the dilator, to the placement location and deployed. The precise location of the filter is followed using external sonography.

The filters described above are very flexible, having low profiles, i.e., small undeployed diameters and short lengths, permitting access to the patient's venous system through various conventional locations, including the jugular vein, the groin vein, etc. Moreover, because the filter features avoid foreshortening of the filter relative to the distal end thereof, highly accurate tracking and placement is achieved by simply visualizing the distal end of the filter as it progresses to the placement location.

Figure 15:
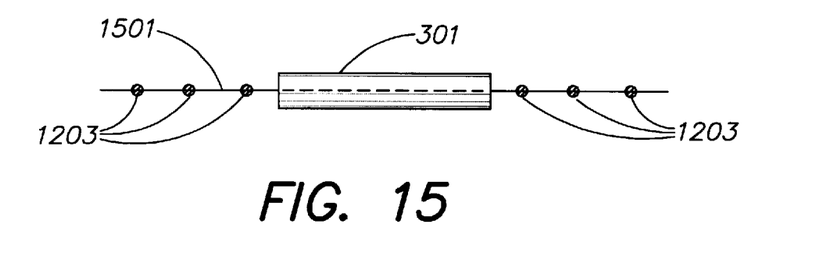
FIG. 15 is a side view of an echogenic tube mounted over a guide or marker wire.

Delivery and deployment of a filter below the renal veins with an echogenic tube 301 instead of or in addition to an echogenic lead 123 proceeds in similar fashion, but with some advantages now described in connection with FIGS. 15–17. Principally, when using a filter configured with an echogenic tube 301, or other configuration of sonographically conspicuous features which are aligned to show the axial alignment and position of the filter, the filter can be slid over a marker wire 1501, as generally shown in FIG. 15 while the true longitudinal position and axial orientation of the filter is correctly visualized.

Figure 16:
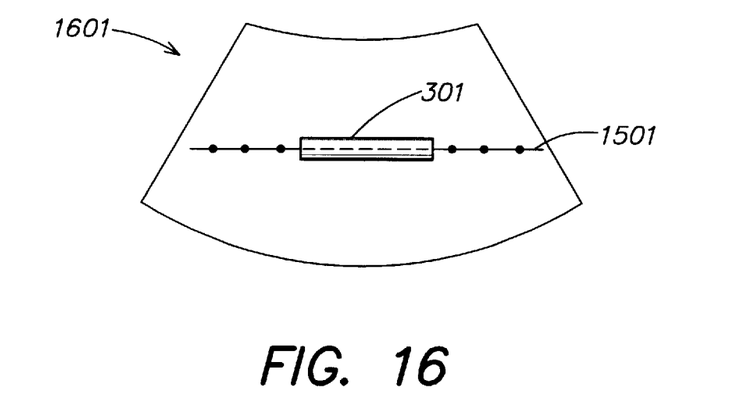
FIG. 16 is a sketch of a true sonographic image of an echogenic tube and guide wire.
Figure 17:
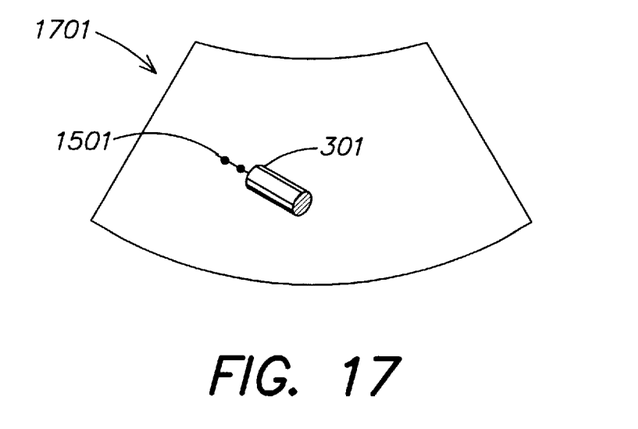
FIG. 17 is a sketch of an oblique sonographic image of an echogenic tube and guide wire.

As shown in the sonographic image sketched in FIG. 16, when the sonographic beam is aligned with the tube 301 and the marker wire 1501, a true image 1601 is obtained, and the true longitudinal and axial position can be determined from the angle of incidence of the beam and the depth of the tube 301 and wire 1501 within the true image 1601. The true image 1601 of FIG. 16 is contrasted with the oblique image 1701 of FIG. 17, in which incomplete information is available. In this oblique image 1701, the angle of incidence of the beam is turned slightly, so that only a portion of tube 301 and marker wire 1501 are each visible in the oblique image 1701. When such an oblique image 1701 presents itself, the surgeon guiding the filter including tube 301 can determine whether the visible portion of tube 301 represents the distal or proximal end of the filter and either guide the filter accordingly or adjust the sonogram beam or the filter position to obtain a true image 1601.

It is expected that struts, and other filter parts which do not specifically include sonographically conspicuous features will be difficult or impossible to see, while the tube 301 will be easily seen. Thus, the tube 301 and marker wire 1501 combine in the image to permit optimum sonographic imaging to be arranged.

The overall filter and placement set and procedures described above permit filter placement by a physician at bedside, in an office (as compared to hospital) setting, or in a sonographic suite. Thus, the need for a fluoroscopic suite or equipment is obviated by the inventive filters, placement sets and methods. The inventive filters, placement sets and methods are also appropriate for intraoperative placement where fluoroscopy is not available, cumbersome, inappropriate or otherwise untenable due to operating room facilities, availability, required procedures or contraindication of any other kind.

When desired, the filters and methods of the present invention can be assisted by magneto-resonant (MR) and computed tomography (CT) visualization methods. Such methods are particularly suitable when the filter is constructed of nitinol or another material which shows up in an MR or CT image. Fluoroscopic assistance can also be used with nitinol filter structures, as well as other materials which show up in a fluoroscopic image. A highly visible marker wire may also be helpful to these methods.

The invention has now been shown and described in connection with an embodiment thereof and some variations, but the invention is not limited thereto. Other variations should now be evident to those skilled in this art, and are contemplated as falling within the scope of the invention which is limited only by the following claims and equivalents thereto.

What is claimed is:

1. A filter, implantable in a blood vessel solely by sonographic visualization, comprising:
   one or more wires arranged to trap blood clots without substantially interfering with normal blood flow; and
   an echogenic feature on at least one wire located in a position which during deployment of the filter remains fixed relative to one end thereof, so the filter position can be accurately determined solely by sonographic visualization.

2. The filter of claim 1, wherein the echogenic feature comprises:
   a bead.

3. The filter of claim 1, wherein the echogenic feature comprises:
   a tube.

4. The filter of claim 3, wherein a marker wire passes through the echogenic tube, the marker wire further comprising:
   a plurality of echogenic markers on the marker wire, whereby correct visualization in a sonogram of a true longitudinal slice along the filter axis is readily ascertainable by presence in the sonogram of the tube in its entirety and each of the plurality of echogenic markers.

5. The filter of claim 3, wherein correct visualization in a sonogram of a true longitudinal slice along the filter axis is readily ascertainable by presence in the sonogram of the tube in its entirety.

6. The filter of claim 1, wherein the one or more wires are arranged to define a cone-shaped basket attached to the echogenic feature at a vertex.

7. The filter of claim 6, wherein the wire is further arranged to define a substantially coplanar flower, the echogenic feature attached thereto at a center thereof.

8. The filter of claim 7, further comprising an outer ring of wire connecting a base of the cone to an outer position of the flower.

9. The filter of claim 6, further comprising:
   a plurality of echogenic markers substantially at a periphery of a base of the cone.

10. The filter of claim 6, further comprising:
    a plurality of loops of wire at a periphery of the basket, whereby the basket is axially aligned thereby during deployment thereof.

11. The filter of claim 6, wherein the basket is defined by substantially radially extending wires.

12. The filter of claim 6, wherein the basket is defined by a mesh of wires extending in both radial directions and directions transverse the radial directions.

13. The filter of claim 1, further comprising:
    a plurality of echogenic markers substantially at a periphery of the filter, whereby deployment thereof can be visualized.

14. A method of implanting a blood filter in a blood vessel, comprising steps of:
    moving a blood filter having an echogenic feature located in a position which during deployment of the filter remains fixed relative to one end thereof through the blood vessel to an implantation site in the blood vessel; and
    during the step of moving, visualizing the echogenic feature of the filter and the implantation site sonographically.

15. The method of claim 14, further comprising:

adjusting a sonographic transducer to correctly visualize in a sonogram a true longitudinal slice along the filter axis, which is readily ascertainable by presence in the sonogram of at least one echogenic feature of the filter.

16. A caval filter placement set, comprising:

a guide wire;

a dilator;

a sheath for introducing the filter; and a caval filter including one or more wires arranged to trap blood clots without substantially interfering with normal blood flow; and an echogenic feature on at least one wire located in a position which during deployment of the filter remains fixed relative to one end thereof, so the filter position can be accurately determined solely by sonographic visualization.

17. The filter of claim 16, the sheath further comprising an echogenic feature at a distal end thereof.

18. The filter of claim 16, the dilator further comprising an echogenic feature at a distal end thereof.

19. The filter of claim 16, the guide wire further comprising plural echogenic features.

20. The filter of claim 19, wherein the guide wire has a hooked end which can engage a renal vein when positioned in the cava.

\* \* \* \* \*